United States Patent [19]
Makino et al.

[11] 3,975,948
[45] Aug. 24, 1976

[54] METHOD OF MEASURING AXIAL FORCE ON A BODY UTILIZING TWO VIBRATION MODES OF ULTRASONIC WAVES

[75] Inventors: Takayuki Makino, Okazaki; Haruhiko Toriyama, Toyota, both of Japan

[73] Assignee: Toyota Jidosha Kogyo Kabushiki Kaisha, Toyota, Japan

[22] Filed: Apr. 24, 1975

[21] Appl. No.: 571,399

[30] Foreign Application Priority Data
Oct. 11, 1974 Japan.............................. 49-116958

[52] U.S. Cl. ................................. 73/67.2; 73/88 F
[51] Int. Cl.² ................. G01H 13/00; G01B 17/04; G01N 29/00
[58] Field of Search ........................... 73/67.2, 88 F

[56] References Cited
UNITED STATES PATENTS
3,306,100    2/1967    Wilhelm et al. ..................... 73/67.2
3,822,587    7/1974    Makino et al........................ 73/67.2
3,918,294    11/1975   Makino et al........................ 73/67.2

Primary Examiner—James J. Gill
Attorney, Agent, or Firm—Cushman, Darby & Cushman

[57] ABSTRACT

A method for measuring the axial force exerted on a body to be measured by applying two ultrasonic frequencies respectively having a transverse-wave vibration mode and a longitudinal-wave vibration mode to a body on which an axial force is exerted, measuring the natural frequencies of the body in the transverse-wave and longitudinal-wave vibration modes, obtaining the result of a computational operation (e.g., the result of a subtraction) on the measured natural frequencies, and measuring from this result the axial force exerted on the body in accordance with the predetermined result-versus-axial force calibration values.

4 Claims, 6 Drawing Figures

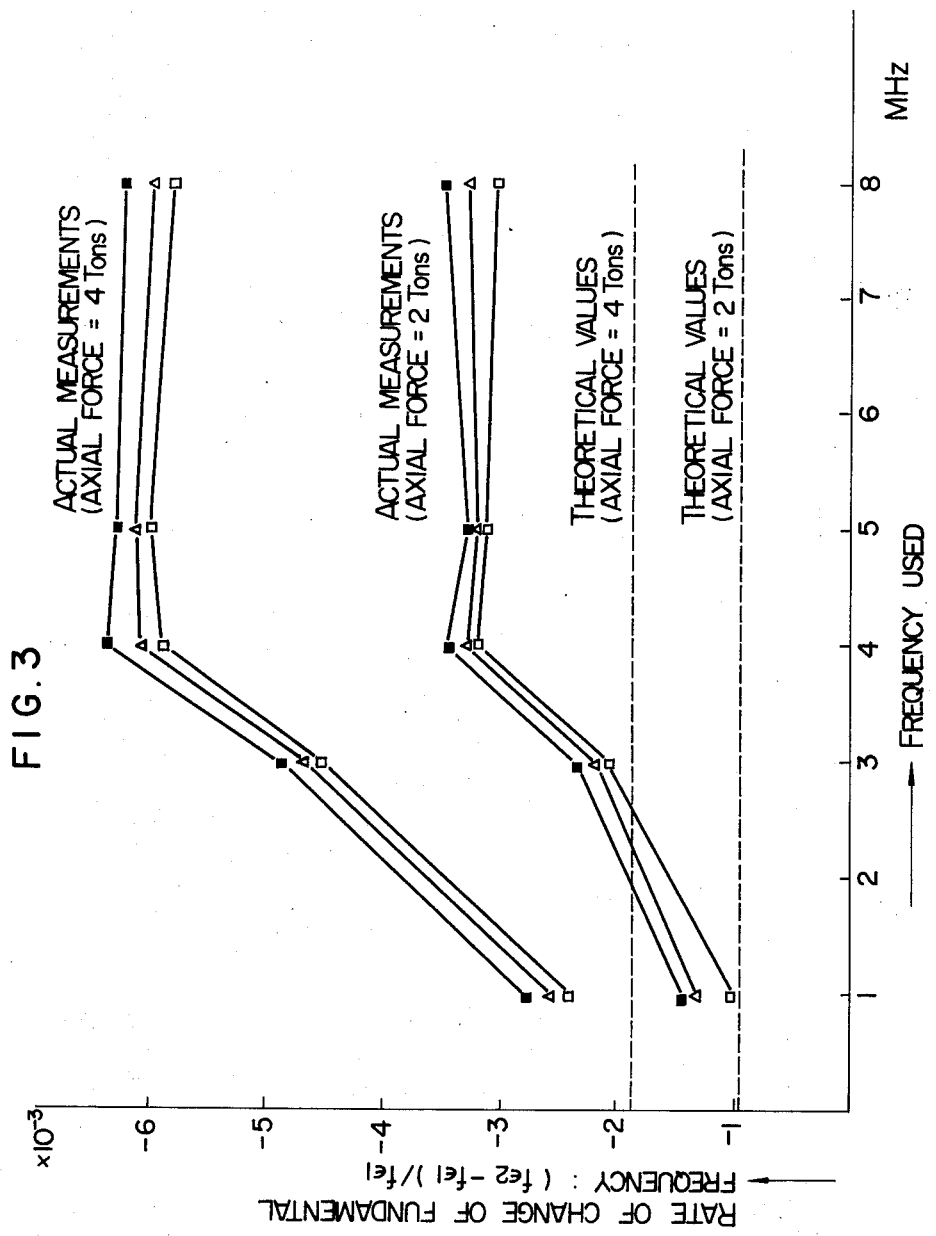

METHOD OF MEASURING AXIAL FORCE ON A BODY UTILIZING TWO VIBRATION MODES OF ULTRASONIC WAVES

The present invention relates to an axial force measuring method which is capable of measuring with ease and in a non-destructive manner the axial force exerted on a body to be measured such as a bolt or the like fitted in position by employing two kinds of ultrasonic waves, i.e., longitudinal and transverse ultrasonic waves having different vibration modes. More particularly, the present invention relates to a non-destructive measuring method which is well suited for use in applications such as the control of axial force on the bolts or the like in process of manufacture and the measurement of the change with time of the axial force on the bolts or the like fitted in position.

With the methods heretofore known in the art for measuring the axial force of bolts, it has been customary to measure the tightening torque of a bolt and make an estimate of the axial force of the bolt on the basis of the measured tightening torque. Generally, the following relation holds between an axial force Q and a tightening torque T of a bolt:

$$Q = 2T/\{d(\mu_s \sec \alpha + \tan \beta) + d_N \mu_N\} \quad (1)$$

where $d$ is the pitch diameter of the thread, $\mu_s$ is the friction coefficient of the thread face, $\alpha$ is the half angle of the thread, $\beta$ is the lead angle of the thread, $d_N$ is the average diameter of the bearing surface of the bolt and $\mu_N$ is the friction coefficient of the bearing surface of the bolt. In other words, it will be seen that even if the tightening torque T of the bolt is fixed, the axial force Q varies depending on the values of the thread face friction coefficient $\mu_S$ or the bearing surface friction coefficient $\mu_N$ of the bolt. Consequently, while it is possible to measure the tightening torque $T$ which is easy to measure, it is impossible to measure the axial force $Q$ as a matter of principle.

Another known type of measuring method employs a resistance wire strain gage to measure the amount of strain produced in a bolt by an axial force and thereby to measure the axial force. A disadvantage of this method is that it is necessary to make a hole in the central part of the bolt and cement the resistance wire strain gage to the inside of the bolt or a specified portion of the base member on which the axial force is exerted must be processed so that the resistance wire strain gage can be cemented for measuring the strain in the bolt, thus making it useful only in applications where the measurement is effected by using a test piece.

It is therefore an object of the present invention to provide an improved method of measuring the axial force of bolts or the like wherein the strain caused in a bolt by an axial force is measured in terms of the change of its natural frequency with the use of two kinds of ultrasonic waves having the longitudinal wave and transverse-wave vibration modes, and the axial force of the bolt is measured from the result of a computational operation on the measured natural frequencies. A unique feature of the improved measuring method is that the ultrasonic natural frequencies are measured in the longitudinal-wave and transverse-wave vibration modes.

The axial force measuring method provided in accordance with the present invention has among its great advantages the fact that it is capable of measuring the axial force exerted on a body to be measured such as a bolt or the like in its fitted position by suitably selectively employing ultrasonic waves having a frequency in a specified frequency range and longitudinal-wave and transverse-wave vibration modes and performing the measurement in a non-destructive manner with ease and high degree of accuracy, thus making the method useful in wide applications such as the process control of the axial force of bolts in process of manufacture and the measurement of the change with time of the axial force on the bolts fitted in position.

Another great advantage of the method of this invention is that since there is a primary relationship between strain and stress within the proportional limit, it is possible to equally measure the axial force, strain or stress of a material in accordance with the difference between the measured ultrasonic natural frequencies, and thus it can be adapted for measuring the distribution of stresses developed in the structural members of a building, automobile, ship, airplane or the like in a non-destructive manner with ease.

The above and other objects, advantages and features of the present invention will become readily apparent from considering the following detailed description in conjunction with the accompanying drawings, in which:

FIG. 3 is an exemplary graph showing the rate of change $(f\epsilon_2 - f\epsilon_1)/f\epsilon_1$ between natural frequencies $f\epsilon_1$ and $f\epsilon_2$ which were obtained by using longitudinal and transverse ultrasonic waves;

Figure 4:
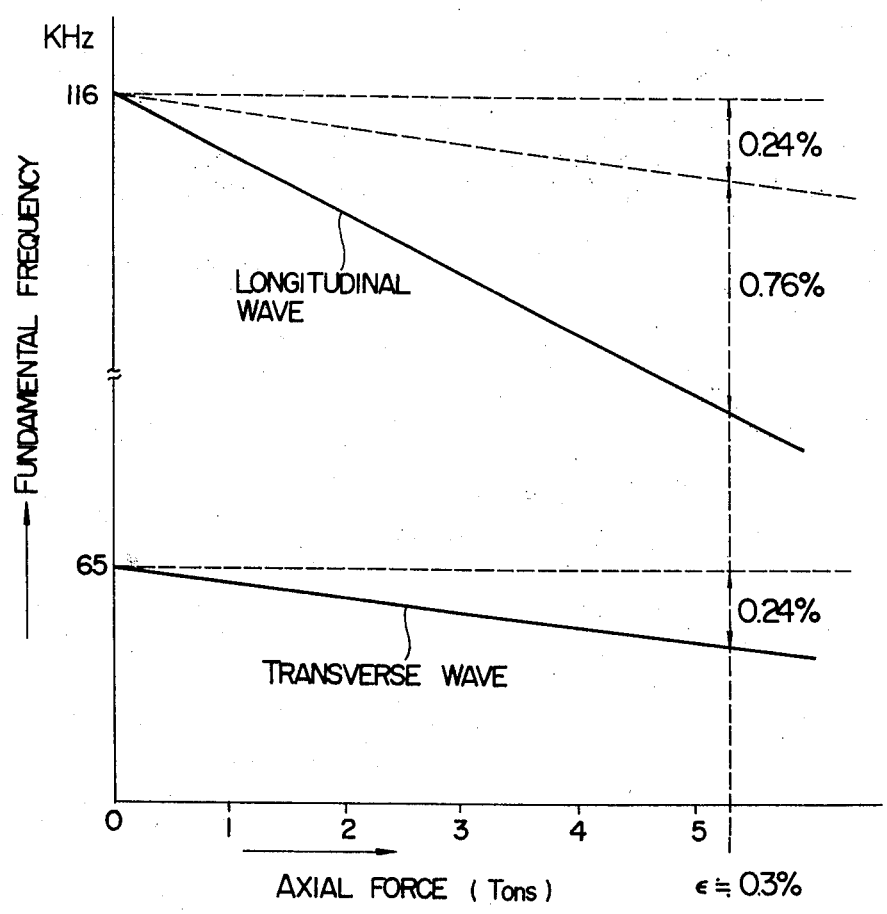
Figure 5:
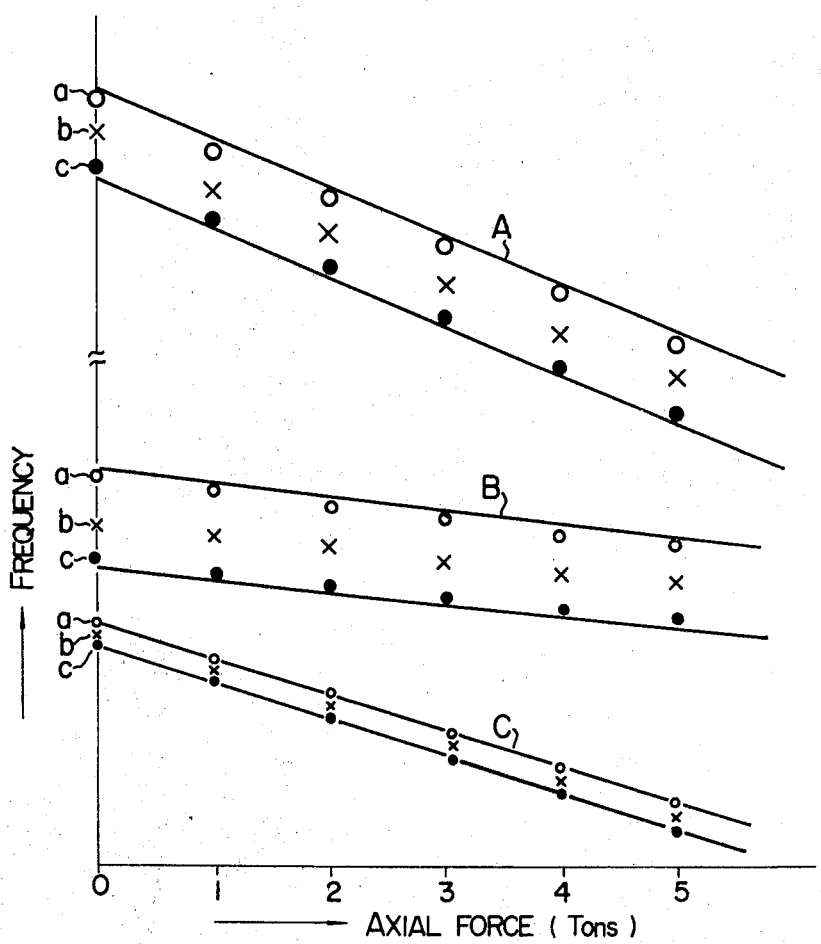

FIG. 4 is an exemplary graph showing the relationship between the axial force and the natural frequency of specified automobile bolts which was obtained by selectively employing the longitudinal and transverse ultrasonic waves; and FIG. 5 is an exemplary graph showing the relationship between the axial force and the natural frequency of the same type of automobile bolts which was obtained by selectively employing the longitudinal and transverse ultrasonic waves.

Figure 1:
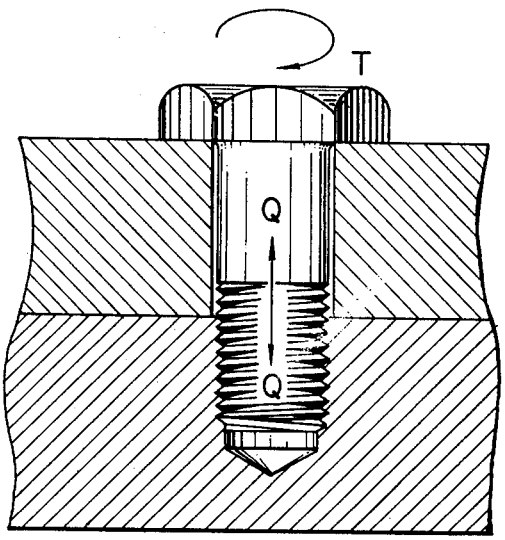
FIG. 1 is a schematic diagram for explaining the relationship between the axial force and the tightening torque of a bolt.
Figure 2A:
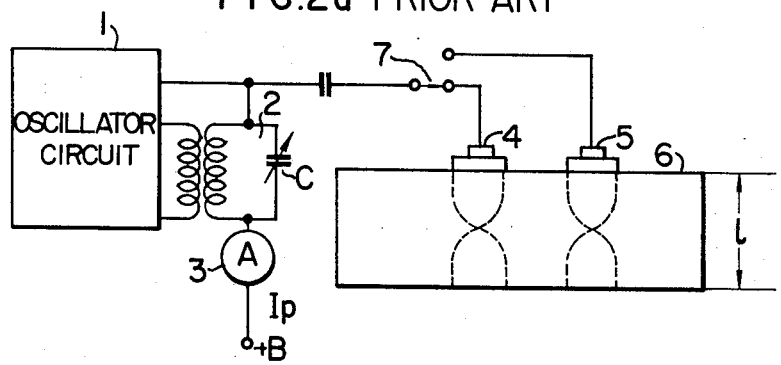
FIG. 2a is a schematic diagram showing one form of a measuring circuit for measuring the required natural frequencies of a body to be measured.
Figure 2B:
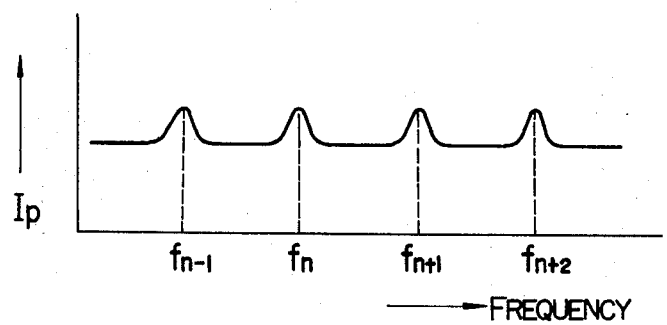
FIG. 2b is a diagram showing the variations of the output current of the oscillator circuit while in resonance.

Referring now to FIGS. 2a and 2b, a customary method of obtaining a natural frequency $f$ of a body to be measured, e.g., the bolt shown in FIG. 1 by employing ultrasonic waves will be described first.

In FIG. 2a, numeral 1 designates an oscillator circuit, 2 a tuning circuit incorporated in the oscillator circuit 1 for changing the oscillation frequency thereof, 3 an ammeter for indicating the magnitude of output current $I_p$ of the oscillator circuit 1, 4 and 5 longitudinal vibration mode and transverse vibration mode ultrasonic resonators which may for example be crystal or barium titanate ceramic resonators, 6 a material to be measured, 7 a switch for selectively actuating the resonators 4 and 5.

When the switch 7 is closed to the lower side so that the output wave of the oscillator circuit 1 is applied to the longitudinal vibration mode ultrasonic resonator 4 causing the latter to radiate the ultrasonic wave to the material 6 and an oscillation frequency $f_C$ is changed by a variable capacitor C of the tuning circuit 2, at an oscillation frequency at which the proper relationship exists between a length L of the material to be measured and the wavelength of the ultrasonic wave in the material, the nodes and loops of the wave oscillating as shown by the dotted line in FIG. 2a are formed at certain points in the material thus causing a simple harmonic motion.

This simple harmonic motion represents the natural vibrations of the material, so that if $l$ is the length of the material and $C_L$ is the propagation velocity of the longitudinal wave in the material, then a natural frequency $f_L$ is generally given by the following equation $$f_L = n \cdot C_L/(2l) \qquad (2)$$

where $n$ is the order of harmonics with $n = 1$ representing the fundamental frequency and $n = 2, 3, \ldots$, representing harmonic frequencies.

The longitudinal-wave natural frequency $f_L$ generated in the manner described above can be measured in terms of the variation of the current value $I_P$ indicated by the ammeter 3 as shown in FIG. 2b. In other words, as the oscillation frequency of the oscillator circuit 1 is varied by the variable capacitor C of the tuning circuit 2, resonance is produced at the natural frequency $f$ of the material and the current $I_P$ increases. Consequently, a fundamental frequency $f_{L1}$ as well as harmonic frequencies $f_{L2}, f_{L3}, \ldots, f_{LN}$ of the material can be easily read directly from the calibration scale of the oscillation frequency $f_C$ preliminarily graduated in relation to the capacitance values of the variable capacitance C. On the other hand, as will be seen from the above equation (2), the fundamental frequency $f_{L1}$ has the following relationship:

$$f_{L1} = f_{L(n+1)} - f_{L(n)} \qquad (3)$$

Therefore, it is possible to obtain the fundamental frequency $f_{L1}$ by measuring the two adjacent harmonic frequencies.

When the switch 7 is closed to the upper side so that the output wave of the oscillator circuit 1 is applied to the transverse vibration mode ultrasonic resonator 5 causing it to radiate the ultrasonic wave to the material 6 and the oscillation frequency $f_C$ is varied by the variable capacitor C of the tuning circuit 2, at an oscillation frequency at which the proper relationship exists between the thickness L of the material and the transverse wave wavelength of the ultrasonic wave in the material, the nodes and loops of the wave oscillating as shown by the dotted line in FIG. 2a are formed at certain positions in the material thus causing a simple harmonic motion.

This simple harmonic motion represents the natural vibrations of the material, so that if $l$ is the length of the material to be measured and $C_S$ is the propagation velocity of the transverse wave in the material, then a natural frequency $f_S$ of the transverse wave is given by the following equation $$f_S = n \cdot C_S/(2l) \qquad (4)$$

where $n$ is the order of harmonics with $n = 1$ representing the fundamental frequency and $n = 2, 3, \ldots$, representing harmonic frequencies.

The natural frequency $f_S$ of the transverse wave obtained in the manner described above can be measured in the similar manner as described in connection with the natural frequency $f_L$ of the longitudinal wave.

Further, while the natural frequencies $f_L$ and $f_S$ of the longitudinal and transverse waves are obtainable respectively from equations (2) and (4), these relationships may be expressed in the following way with $n = 1$. In the case of longitudinal wave, we obtain $$f_L = C_L/2l = \sqrt{E/\rho}/2l = \sqrt{EV/M}/2l \qquad (5)$$

In the case of transverse wave, we obtain $$f_S = C_S/2l = \sqrt{G/\rho}/2l = \sqrt{GV/M}/2l \qquad (6)$$

where $E$ is the longitudinal modulus, $\rho$ the density, $M$ the mass, $V$ the volume and $G$ the transverse modulus. In other words, it will be seen that the natural frequency $f$ is inversely proportional to the length $l$ of the material, while it is proportional to the square root of the volume $V$ and the longitudinal modulus E or the transverse modulus G.

Next, the variations of the natural frequency caused by the strains produced in a body to be measured will be considered. For example, when a load is applied to a cylindrical body thus causing a tensile strain $\epsilon$ in the body, the rate of change of natural frequency before and after the production of the tensile strain $\epsilon$ will be given as follows, with the longitudinal modulus $E$, the transverse modulus $G$ and the mass $M$ being constant and irrespective of the longitudinal wave or the transverse wave $$(f_\epsilon - f_o)/f_o = \{\sqrt{V_\epsilon/V_o}/(l_\epsilon - l_o)\} - 1 = \{(1-\gamma\epsilon)/\sqrt{1+\epsilon}\} - 1 \qquad (7)$$

where $f_o$ and $f_\epsilon$ are respectively the natural frequencies before and after the production of the strain $\epsilon$ in the cylinder, $V_o$, $V_\epsilon$ and $l_o$, $l_\epsilon$ are similarly the volumes and lengths of the cylinder before and after the production of the strain $\epsilon$, and $\gamma$ is the Poisson's Ratio.

Assuming that the tensile strain produced in the cylinder is 0.3%, then with the Poisson's Ratio $\gamma = 0.29$ the rate of change of natural frequency is given by the following equation $$(f - f_o)/f_o = \{(1-0.29 \times 0.003)/\sqrt{1+0.003}\} - 1 = -0.00237 \text{ (or } -0.0024, \text{ rounded off)} \qquad (8)$$

In other words, the production of the tensile strain of 0.3% causes the natural frequency to decrease by about 0.24%.

On the other hand, where strains $\epsilon_1(\epsilon_1 \geq 0)$ and $\epsilon_2(\epsilon_2 > 0)$ are produced by the application of external forces, the rate of change of frequency between the natural frequencies $f\epsilon_1$ and $f\epsilon_2$ will be given by the following equation irrespective of the longitudinal wave or the transverse wave:

$$(f\epsilon_2 - f\epsilon_1)/f\epsilon_1 = K[\{(1-\gamma\epsilon_2)\sqrt{1+\epsilon_1}/(1-\gamma\epsilon_1)\sqrt{1+\epsilon_2}\} - 1] \qquad (9)$$

where the constant $K = 1$ as will be seen from equation (7).

In the course of the analytical study of the corresponding relationship between the theoretical values and the experimental values on the basis of the above-described theoretical ground, it was confirmed that an entirely new phenomenon occurred depending on the vibration mode and frequency band of the ultrasonic wave used. In other words, while the relationship of the above-mentioned equation (8) substantially held when the longitudinal waves of a ultrasonic frequency band of below 2 to 3 MHz and the transverse waves of a ultrasonic frequency band ranging from 0.5 to 10 MHz were employed, it was confirmed that with the longitudinal waves of a ultrasonic frequency band greater than several MHz the values of $(f_\epsilon - f_o)/f_o$ became considerably greater than those obtained from the theoretical equation ($K>1$ in equation (9)).

FIG. 3 is a graph showing the rate of change of frequency $(f_{\epsilon_2} - f_{\epsilon_1})/f_{\epsilon_1}$ between the natural frequencies $f_{\epsilon_1}$ and $f_{\epsilon_2}$ which were obtained on three ring gear set bolts for automobiles (the actual measurements data of the three bolts are indicated at □, Δ and ■ ). In FIG. 3, the ordinate shows a scale of the rates of change of frequency and the abscissa shows a scale of ultrasonic frequencies used.

It will be seen from FIG. 3 that in the case of the working frequencies higher than 4 MHz the rate of change of frequency was almost constant, while the average change rate was 0.32% according to the actual measurements obtained with the axial force of 2 tons and the average change rate was 0.61% according to the actual measurements obtained with the axial force of 4 tons.

On the other hand, the dotted lines in FIG. 3 shows the theoretical values of the rate of change of frequency obtained from equation (7), and it will be seen that the change rate averaged 0.089% when the axial force was 2 tons and the average change rate was 0.178% when the axial force was 4 tons.

It will thus be seen that where the longitudinal ultrasonic waves having a frequency higher than 4 MHz were used, the measured values of the change rate of frequency were as high as about 3.5 times the theoretical values. This means that the constant $K$ equation (9) is equivalent to 3.5.

On the other hand, it was confirmed that the actual measurements of the rate of change of frequency $(f_{\epsilon_2} - f_{\epsilon_1})/f_{\epsilon_1}$ between $f_{\epsilon_1}$ and $f_{\epsilon_2}$ obtained on the three bolts showed that the actual measurements obtained by using the transverse ultrasonic frequency band ranging from 0.5 to 10 MHz approximated the theoretical values shown by the dotted lines in FIG. 3. Therefore, no graphical representation of these actual measurements is shown.

The results of the experiments made on automobile bolts will be described by way of example hereunder.

In FIG. 4 illustrating the exemplary results of the experiments made on automobile ring gear set bolts (diameter = 11 $\phi$, length = 25 mm) by employing longitudinal and transverse waves having a ultrasonic frequency of 5 MHz, the abscissa shows a scale of axial forces and the ordinates shows a scale of fundamental frequencies. The ordinate is scaled in KHz inasmuch as the determination of fundamental frequencies in accordance with equation (3) above produces results in KHz units. It will be seen from FIG. 4 that the experimental values obtained by using the transverse wave were substantially equal to the values of the rate of change of natural frequency obtained from the above equation (8), whereas the experimental values obtained by using the longitudinal wave were considerably higher than the values of the rate of change of natural frequency obtained from the theoretical equation.

In other words, where the axial force was zero the rate of change of natural frequency measured by using the longitudinal wave was higher by about 20% than that obtained by using the transverse wave, whereas when there was a strain of 0.3% (corresponding to an axial force of 5.3 tons) the rate of change of natural frequency was about 1% which was considerably higher than the value of 0.24% obtained from the theoretical equation. This indicates that the value of K in equation (9) is on the order of 4, and it was confirmed that the use of the longitudinal waves in the ultrasonic frequency range higher than several MHz presented a phenomenon in which the value of the propagation velocity $C_L$ in the body to measured considerably decreased as the magnitude of the strain increased. This phenomenon was confirmed by fully studying the results of the experiments conducted on various types of bolts.

Referring to FIG. 5 showing an example of the measurements of the relationship between axial force and natural frequency which were made on 50 pieces of automobile ring gear set bolts by using the longitudinal and transverse waves having a ultrasonic frequency of 5 MHz, the ordinate shows a scale of natural frequencies (fundamental frequencies) and the abscissa is graduated with the scale of the conventionally used axial force tester (the accuracy of measurement is ± 1%). In FIG. 5, letters A and B respectively show the data measured by using the longitudinal and transverse waves, and C shows an exemplary graph of the values obtained by subtracting the data B from the data A. The data of the three representative bolts distributed respectively at the upper, middle and lower limits of the respective graphs are designated by marks ○, X and ● .

While the variations in the values as shown by the bolts a, b and c in FIG. 5 may be presumed as caused by the variations in the length, heat treatment conditions, composition, etc. of the bolts, such variations tend to exist irrespective of whether the longitudinal wave or the transverse wave is used. Consequently, these variations may be reduced to a considerable extent by graphically representing the differences between the values obtained by using the longitudinal wave and those obtained by using the transverse wave on the respective bolts as shown at C in FIG. 5. While the differences between A and B are shown at C in FIG. 5, the similar results may be obtained by obtaining the change rate (A − B)/A, and the effects of the variations among the bolts may be reduced to a greater extent by using the change rate.

Utilizing the technique which has been described, axial force measurements accurate to ± 0.3 ton can be achieved.

It will thus be seen from the foregoing description that by measuring the natural frequencies by means of the longitudinal and transverse ultrasonic waves, respectively, and obtaining the results of a computational operation (e.g., the operation of subtraction) on the measured natural frequencies, it is possible to directly read the value of axial force on a bolt from the calibration curve preliminarily constructed on the same kinds of bolts.

In other words, there is no need to preliminarily measure the natural frequencies of bolts prior to their tightening, and it is possible to easily and non-destructively measure as desired the axial force of the bolts which have been fitted in positions. Thus, the method of this invention has a very wide range of applications.

What is claimed is:

1. In an axial force measuring method for measuring the axial force on a body to be measured by measuring the natural frequencies of said body through the forced oscillation thereof caused by ultrasonic waves and measuring the rate of change of said measured natural frequencies where a relationship $(f\epsilon_2 - f\epsilon_1)/f\epsilon_1 = K[\{(1-\gamma\epsilon_2) \sqrt{1+\epsilon_1}/(1-\epsilon_1) \sqrt{1+\epsilon_2}\}-1]$ (where $\gamma$ is the Poisson's Ratio) is held between natural frequencies $f\epsilon_1$ and $f\epsilon_2$ of said body existing when a strain $\epsilon_1(\epsilon_1 \geqq 0)$ and another strain $\epsilon_2(\epsilon_2 > 0)$ are respectively produced in said body, said method comprising the steps of selecting a first ultrasonic frequency having a transverse-wave vibration mode for establishing $K = 1$ in said relationship and a second ultrasonic frequency having a longitudinal-wave vibration mode for establishing $K > 1$ in said relationship, using said ultrasonic frequencies for respectively measuring the natural frequency of said body existing when an axial force is exerted thereon, performing a computational operation on said measured natural frequencies, and measuring the axial force exerted on said body from the result of said computational operation in accordance and with a predetermined result-versusaxial force calibration value.

2. A method according to claim 1, wherein the result of said computational operation is the difference between said measured natural frequencies.

3. A method according to claim 1, wherein the result of said computational operation is the value of rate of change between said measured natural frequencies.

4. A method according to claim 1, wherein said body to be measured is an automobile bolt.

* * * * *